(12) United States Patent
Tan et al.

(10) Patent No.: US 11,523,868 B2
(45) Date of Patent: Dec. 13, 2022

(54) BONE REGISTRATION METHODS FOR ROBOTIC SURGICAL PROCEDURES

(71) Applicant: THINK SURGICAL, INC., Fremont, CA (US)

(72) Inventors: Yiyong Tan, Fremont, CA (US); Randall Hanson, Fremont, CA (US); Aruna Gummalla, Fremont, CA (US)

(73) Assignee: Think Surgical, Inc., Fremont, CA (US)

( * ) Notice: Subject to any disclaimer, the term of this patent is extended or adjusted under 35 U.S.C. 154(b) by 102 days.

(21) Appl. No.: 16/835,800

(22) Filed: Mar. 31, 2020

(65) Prior Publication Data

US 2020/0305978 A1 Oct. 1, 2020

Related U.S. Application Data (60) Provisional application No. 62/827,567, filed on Apr. 1, 2019.

(51) Int. Cl.
| | |
|---|---|
| *A61F 5/00* | (2006.01) |
| *A61B 34/10* | (2016.01) |
| *A61B 17/17* | (2006.01) |
| *A61B 34/30* | (2016.01) |
| *A61B 17/16* | (2006.01) |
| *A61B 90/00* | (2016.01) |
| *A61B 34/00* | (2016.01) |

(52) U.S. Cl.
CPC .......... *A61B 34/10* (2016.02); *A61B 17/1703* (2013.01); *A61B 17/1764* (2013.01); *A61B 17/1675* (2013.01); *A61B 34/30* (2016.02); *A61B 2034/104* (2016.02); *A61B 2034/105* (2016.02); *A61B 2034/252* (2016.02); *A61B 2090/364* (2016.02); *A61B 2090/3762* (2016.02)

(58) Field of Classification Search
CPC combination set(s) only.
See application file for complete search history.

(56) References Cited

U.S. PATENT DOCUMENTS

2007/0270685 A1* 11/2007 Kang ..................... A61B 34/76
600/424

* cited by examiner

*Primary Examiner* — Sameh R Boles
(74) *Attorney, Agent, or Firm* — Blue Filament Law PLLC (57) ABSTRACT

A computer-implemented method to improve the point collection process during registration of a bone for a computer-assisted surgical procedure is provided. Based on bone digitization data, a simulation is performed to confirm the accuracy of the registration for different digitization regions. Results are tested to identify which digitization regions meet a predefined accuracy requirement. The resulting information is used to perform a computer-assisted surgical procedure. A computerized simulation method for registration of a bone for a computer-assisted surgical procedure is also provided based on processor executing random stroking an expected exposed surface of a bone model with multiple of stroke curves to cover most of the bone model surface with uniform noise and a random sample consensus is applied to remove outlying point to yield the best registration results, to find the top subset as to overlap. A method to perform computer-assisted surgery is also provided.

16 Claims, 7 Drawing Sheets

BONE REGISTRATION METHODS FOR ROBOTIC SURGICAL PROCEDURES

RELATED APPLICATIONS

This application is a non-provisional application that claims priority benefit of U.S. Provisional Application Ser. No. 62/827,567 filed Apr. 1, 2019; the contents of which are hereby incorporated by reference.

TECHNICAL FIELD

The present invention generally relates to bone registration for computer-assisted orthopedic surgery, and more particularly to improved and less invasive registration methods.

BACKGROUND

Computer-assisted orthopedic surgery is an expanding field having applications in total joint arthroplasty (TJA), bone fracture repair, maxillofacial reconstruction, and spinal reconstruction. For example, the TSOLUTION ONE® Surgical System (THINK Surgical, Inc., Fremont, Calif.) aids in the planning and execution of total hip arthroplasty (THA) and total knee arthroplasty (TKA). The TSOLUTION ONE® Surgical System includes: a pre-operative planning software program to generate a surgical plan using an image data set of the patient's bone and computer-aided design (CAD) files of several implants; and an autonomous surgical robot that precisely mills the bone to receive an implant according to the surgical plan. In order for the computer-assisted surgical system to accurately prepare a bone, the bone needs to be registered to the surgical system. Registration maps the surgical plan to the spatial position and orientation (POSE) of the bone in a coordinate system of the surgical system.

Several registration procedures are known in the art, illustratively including pin-based, point-to-point matching, point-to-surface matching, laser scanning, and image-free registration, as described in U.S. Pat. Nos. 5,951,475; 6,033,415; 8,287,522; and 8,010,177. The most commonly used registration procedure relies on the manual collection of several points (i.e., point-to-point, point-to-surface) on the bone using a tracked digitizer probe. The collected/digitized points are matched to corresponding surfaces on the image of the bone using various best-fit algorithms such as iterative closest point (ICP). This matching procedure transforms the image of the bone (and therefore the surgical plan) into the coordinate system of the surgical system to allow a surgical device to accurately execute the plan on the bone. However, the point-to-point and point-to-surface registration procedures are particularly tedious, time consuming, and requires a high-level of hand-eye coordination. For one, the user has to look at a display monitor (displaying the location of the points on a virtual model of a bone) to identify where each point needs to be collected on the actual bone. The user then has to locate that corresponding point on the actual bone to collect the point. The user's eyes and attention are constantly moving between the monitor and the bone during registration. In addition, the user has to accurately identify the specific location of each point on the bone as displayed on the bone model, which can be up to 45 different points to accurately register the bone. This may be particularly difficult as the bone is minimally exposed and usually covered by biological fluids and/or tissues. This can lead to the miscollection of one or more points, which may affect registration accuracy.

Further, at least some of the registration points need to be digitized in more risk prone areas. For example, in TKA, points need to be collected in an unexposed proximal region of the femur and an unexposed distal region of the tibia. These unexposed regions are referred to herein as band points. To digitize these points, either an incision is made, or a percutaneous probe is used to pierce through the skin. This may pose an additional risk to the patient and can further increase the surgical time.

Thus, there exists a need in the art for a system and method to improve the point collection process during bone registration for computer-assisted surgical procedures.

SUMMARY OF THE INVENTION

A computer-implemented method to improve the point collection process during registration of a bone for a computer-assisted surgical procedure is provided. A processor executes selection of a first set of digitization regions on the bone based on expected exposed regions of the bone. A software based simulation is performed to confirm the accuracy of the registration when digitizing points in the first set of digitization regions. A second set of digitization regions is selected on a different region of the bone based on expected exposed regions of the bone and a second software is performed based simulation to confirm the accuracy of the registration when digitizing points in the second set of digitization regions. The selecting and performing are repeated on different sets of digitization regions or combinations of digitization regions that are exposed, and testing to identify which digitization regions meet a predefined accuracy requirement. The resulting information is used to perform a computer-assisted surgical procedure.

A computerized simulation method for registration of a bone for a computer-assisted surgical procedure is also provided based on processor executing random stroking an expected exposed surface of a bone model with multiple of stroke curves to cover most of the bone model surface. A subset of stroke curves are selected from the multiple stroke curves, and for each selected stroke curve, a sample of multiple points is used. Uniform noise is added to the multiple points, and a random sample consensus (RANSAC algorithm) is applied to remove outlying points from the multiple points. A curve analysis is performed to select a subset of points from the remaining multiple points which can yield the best registration results. Several of these steps are repeated for all subsets of stroke curves from which at least two top subsets of stroke curves are selected that yield the best registration results. A selection is made among the top subsets of a stroke curve set having the most overlap over an exposed region during surgery.

A method to perform computer-assisted surgery is also provided that includes obtaining pre-operative bone data of a bone. A surgical procedure is planned relative to the pre-operative bone data, where the planning defines a set of surgical device operational data relative to the pre-operative bone data. The operational data is registered onto the bone by collecting a multiple points on the bone with a digitizer in the bone regions identified by an above-detailed method of point collection or simulation. The resulting operational data is provided to computer-assisted surgical device for implementing the cutting of bone.

BRIEF DESCRIPTION OF THE DRAWINGS

The present invention is further detailed with respect to the following drawings that are intended to show certain aspects of the present of invention, but should not be construed as a limit on the practice of the invention, wherein:

FIGS. 6A-6D graphically illustrate the method of FIG. 5 in accordance with embodiments of the invention, where

DETAILED DESCRIPTION

The present invention has utility as a system and method to improve the point collection process during registration for computer-assisted surgical procedures. Embodiments of the invention provide a method to improve the registration process by identifying a plurality of optimal regions or contours on a bone to digitize that achieves an accurate registration while greatly reducing the complexity and time required for the digitizing process, as well as lessening the risks to patients during a surgical procedure. By identifying these optimal regions, the more risk prone areas (band points) can be avoided during the registration process, and in some aspects of the invention, the collection of points is no longer needed but rather, three or more lines along the identified contours can be used to register the bone.

The present invention will now be described with reference to the following embodiments. As is apparent by these descriptions, this invention can be embodied in different forms and should not be construed as limited to the embodiments set forth herein. Rather, these embodiments are provided so that this disclosure will be thorough and complete, and will fully convey the scope of the invention to those skilled in the art. For example, features illustrated with respect to one embodiment can be incorporated into other embodiments, and features illustrated with respect to a particular embodiment may be deleted from the embodiment. In addition, numerous variations and additions to the embodiments suggested herein will be apparent to those skilled in the art in light of the instant disclosure, which do not depart from the instant invention. Hence, the following specification is intended to illustrate some particular embodiments of the invention, and not to exhaustively specify all permutations, combinations, and variations thereof.

Further, it should be appreciated that although the systems and methods described herein make reference to the knee, the systems and methods may be applied to other bones and joints in the body illustratively including the hip, ankle, elbow, wrist, skull, and spine, as well as revision of initial repair or replacement of any of the aforementioned bones or joints.

Furthermore, it should be appreciated that while several steps performed by an inventive process involve one or more abstract ideas, the present invention as a whole includes aspects that amount to significantly more than the abstract idea. Indeed, aspects of the present invention have never been previously performed in manual or digital form prior to the present invention. Embodiments of the invention employ the use of computer models and algorithms to make computational decisions that improve the registration process by identifying multiple optimal regions or contours on a bone to digitize that achieves an accurate registration while greatly reducing the tediousness and time required for the digitizing process, as well as lessening the risks to patients during a surgical procedure. By identifying these optimal regions, the more risk prone areas (band points) can be avoided during the registration process, and in some aspects of the invention, the collection of points is no longer needed but rather three or more lines along the identified contours can be used to register the bone.

These aspects of the invention provide results that are significantly more than implementing an abstract idea on a computer.

The invention relates to software technology that provides an end user with a graphical user interface (GUI) from a platform, where the platform receives information about a patient's bone structure to guide a computer-assisted surgical procedure in assisting a surgeon during a surgical procedure by providing orientation information about the bone(s) involved in the surgical procedure to a computer-assisted surgical device. Accordingly, the inventive steps do not recite an abstract idea nor do they implicate any other judicial exception.

It is to be understood that in instances where a range of values are provided that the range is intended to encompass not only the end point values of the range but also intermediate values of the range as explicitly being included within the range and varying by the last significant figure of the range. By way of example, a recited range of from 1 to 4 is intended to include 1-2, 1-3, 2-4, 3-4, and 1-4.

Unless otherwise defined, all technical and scientific terms used herein have the same meaning as commonly understood by one of ordinary skill in the art to which this invention belongs. The terminology used in the description of the invention herein is for the purpose of describing particular embodiments only and is not intended to be limiting of the invention.

Unless indicated otherwise, explicitly or by context, the following terms are used herein as set forth below.

As used in the description of the invention and the appended claims, the singular forms "a," "an" and "the" are intended to include the plural forms as well, unless the context clearly indicates otherwise.

Also as used herein, "and/or" refers to and encompasses any and all possible combinations of one or more of the associated listed items, as well as the lack of combinations when interpreted in the alternative ("or").

As used herein, the term "pre-operative bone data" refers to bone data used to pre-operatively plan a procedure before making modifications to the actual bone. The pre-operative bone data may include one or more of the following: an image data set of a bone (e.g., acquired via computed tomography (CT), magnetic resonance imaging (MRI), ultrasound, x-ray, laser scan, etc.), a virtual generic bone model, a physical bone model, a virtual patient-specific bone model generated from an image data set of a bone, a set of data collected directly on a bone intra-operatively (commonly used with imageless computer-assist devices), etc.

As used herein, the term "digitizer" refers to a device capable of measuring, collecting, and/or recording physical coordinates in three-dimensional space. For example, the 'digitizer' may be: a "mechanical digitizer" having passive links and joints, such as the high-resolution electro-mechanical sensor arm described in U.S. Pat. No. 6,033,415; a non-mechanically tracked digitizer probe (e.g., optically tracked, electromagnetically tracked, acoustically tracked, and equivalents thereof) as described for example in U.S. Pat. No. 7,043,961; or an end-effector of a robotic device.

As used herein, the term "digitizing" refers to the collecting, measuring, and/or recording of physical points in space with a digitizer.

As used herein, the term "registration" refers to the determination of the POSE and/or coordinate transformation between two or more objects or coordinate systems such as a computer-assist device, a bone, pre-operative bone data, surgical planning data (i.e., an implant model, cut-file, virtual boundaries, virtual planes, cutting parameters associated with or defined relative to the pre-operative bone data), and any external landmarks (e.g., a tracking array) associated with the bone, if such landmarks exist. Conventional methods of registration known in the art are described in U.S. Pat. Nos. 6,033,415; 8,010,177; and 8,287,522.

Also described herein are "computer-assisted surgical systems (or devices)." A computer assisted surgical system refers to any system requiring a computer to aid in a surgical procedure. Examples of computer-assisted surgical systems include tracking systems, tracked passive instruments, active or semi-active hand-held surgical devices and systems, autonomous serial-chain manipulator systems, haptic serial chain manipulator systems, parallel robotic systems, or master-slave robotic systems, as described in U.S. Pat. Nos. 5,086,401; 7,206,626; 8,876,830; and 8,961,536; U.S. Pat. App. No. 2013/0060278, and PCT. Intl. App. No. US2016/051713. In particular embodiments, the surgical system is a robotic surgical system as described below.

Figure 1:
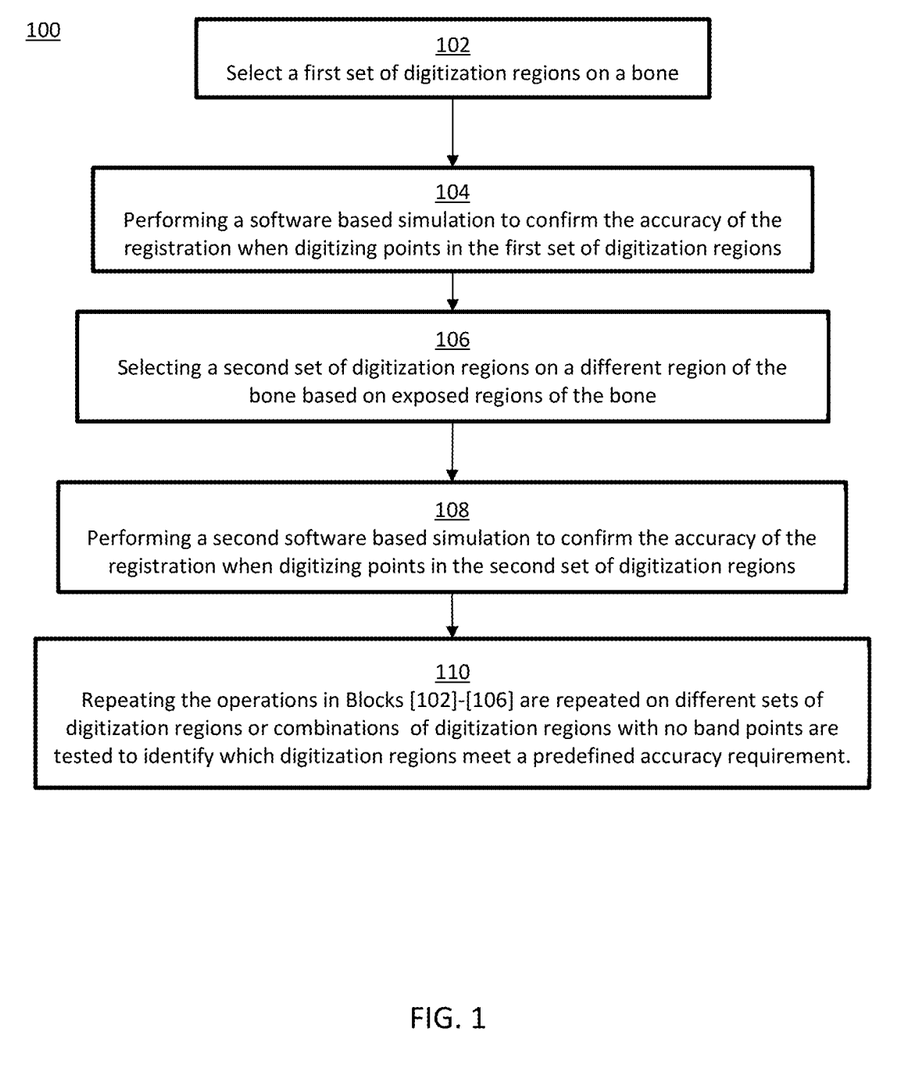
FIG. 1 depicts a method to improve the point collection process during bone registration in accordance with embodiments of the invention.

With reference now to the drawings, FIG. 1 depicts an embodiment of a method 100 to improve the point collection process during bone registration. A first set of digitization regions are initially chosen based on expected exposed regions of the bone (no band points), Block 102. Performing a software based simulation to confirm the accuracy of the registration when digitizing points in the first set of digitization regions, Block 104. The simulation accounts for the various errors that may occur during the entire process including image processing errors, segmentation errors, encoder errors, the presence of soft tissue, digitizing errors, etc. Selecting a second set of digitization regions on a different region of the bone based on expected exposed regions of the bone (no band points), Block 106. Performing a second software-based simulation to confirm the accuracy of the registration when digitizing points in the second set of digitization regions, Block 108. The operations in Blocks 102-106 are repeated on different sets of digitization regions or combinations of digitization regions with no band points to identify which digitization regions meet a predefined accuracy requirement. The simulations are performed on multiple cadaver cases using a large number of trials to emulate point collection by different users, Block 108.

Figure 2A:
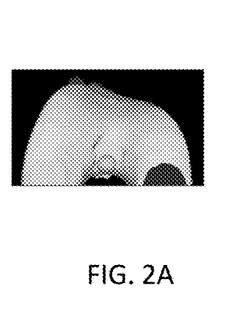
FIGS. 2A-2O illustrate points and regions on a simulated bone model required for TKA femur registration in accordance with embodiments of the invention.
Figure 2B:
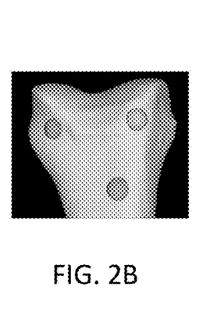
Figure 2C:
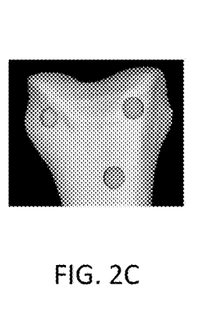
Figure 2D:
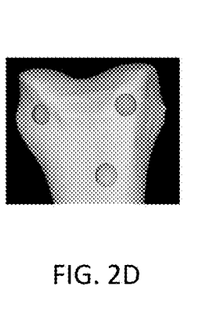
Figure 2E:
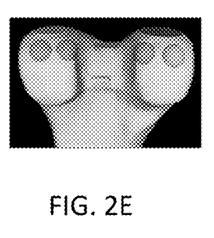
Figure 2F:
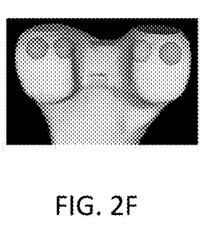
Figure 2G:
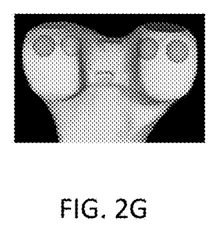
Figure 2H:
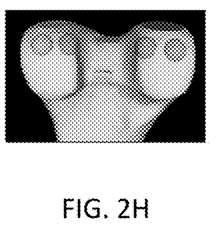
Figure 2I:
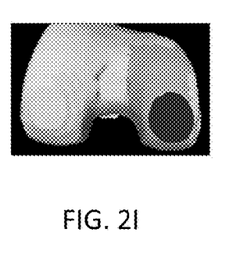
Figure 2J:
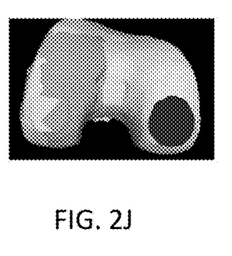
Figure 2K:
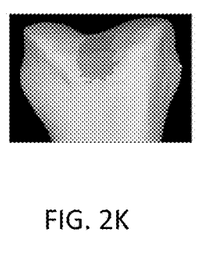
Figure 2L:
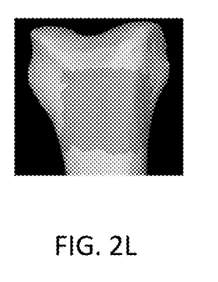
Figure 2M:
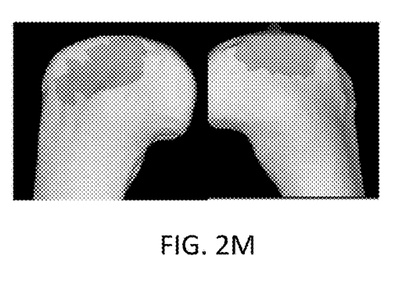
Figure 2N:
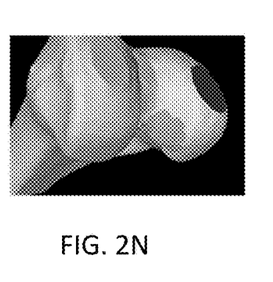
Figure 2O:
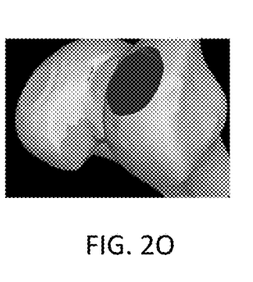
Figure 3A:
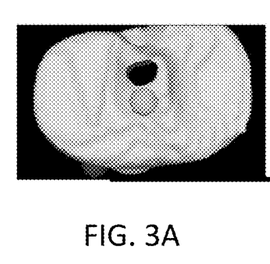
FIGS. 3A-3K illustrate points and regions on a simulated bone model required for TKA tibia registration in accordance with embodiments of the invention.
Figure 3B:
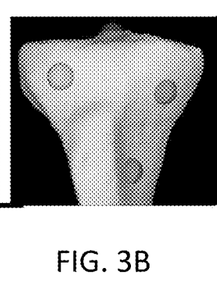
Figure 3C:
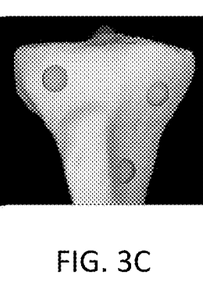
Figure 3D:
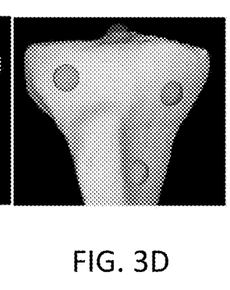
Figure 3E:
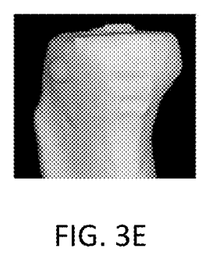
Figure 3F:
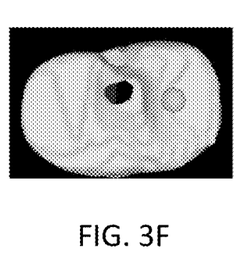
Figure 3G:
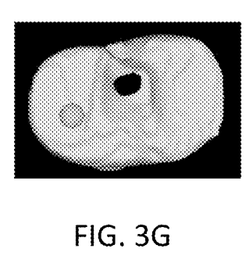
Figure 3H:
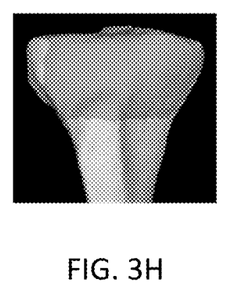
Figure 3I:
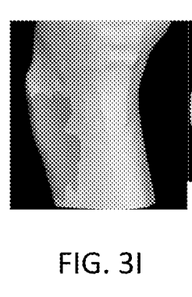
Figure 3J:
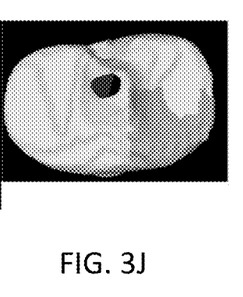
Figure 3K:
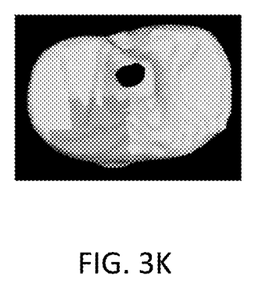

In a specific inventive embodiment, TKA femur registration uses three initial points that are located on the intercondylar notch (FIG. 2A), anterolateral and anteromedial trochlear ridge to perform an initial alignment (FIGS. 2B-2D). Afterwards, the registration method collects more points to calculate the digitizer to pre-operative bone data (e.g., CT data) matrix (FIGS. 2E-2H). In total, 40 points are collected to calculate the registration matrix. Shown in FIGS. 2I-2O, the identified regions used in the TKA femur registration are the shaded portions of the bone.

FIGS. 3A-3K illustrate TKA tibia registration that in specific inventive embodiments may also employ the use of three initial points to perform an initial alignment (FIGS. 3B-3D) as was the case with femur registration shown in FIGS. 2B-2D. Subsequently, embodiments of the inventive registration method collect more points to calculate the digitizer to pre-operative bone data matrix. In a specific inventive embodiment, a total of 35 points are collected to calculate the registration matrix. The shaded regions in FIGS. 3G-3K illustrate the identified regions in the TKA tibia registration.

In inventive embodiments, the POSE of a bone is simulated randomly with the rotation angles of the bone limited to −179 degrees to 180 degrees about all three coordinate axes (X, Y, Z), and the translation movement of the bone is limited to ±500 mm with respect to the digitizer's base along all three coordinate axes.

Figure 4:
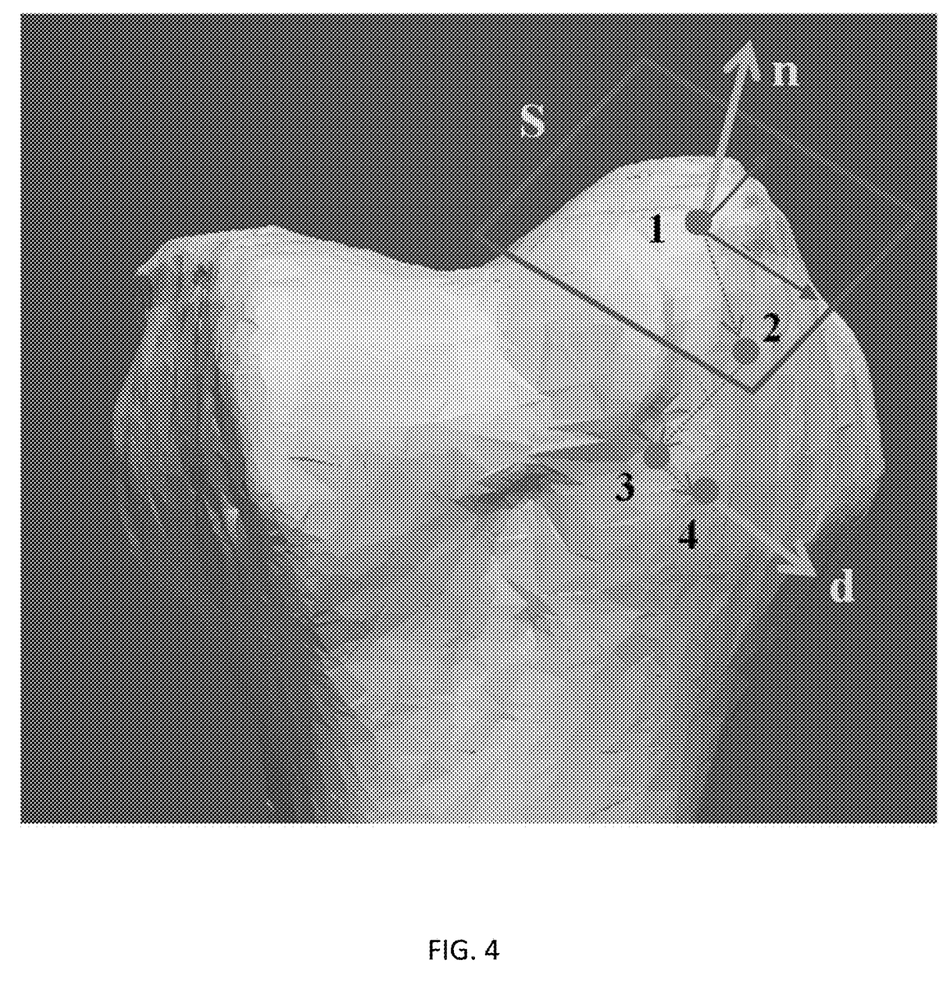
FIG. 4 depicts a simulated bone model and an inventive process of generating a simulated digitizer point, where Point 1 is an ideal point on the bone surface, Point 2 is created by moving point 1 randomly in a plane with the normal perpendicular to the bone surface, Point 3 is the closest point on the bone surface to point 2, and Point 4 is the simulated digitizer point that is the noisy version of point 3.

In embodiments of the inventive method, the bone surface points to be digitized are simulated by adding random noise to the ideal region points on the bone surface model (point 1 in FIG. 4). This added random noise simulates the uncertainty introduced by the user and is assumed to have a uniform distribution with a minimum value of −10 mm and a maximum value of 10 mm. The point on the bone surface (point 1) is moved by a random number chosen from a uniform distribution on a plane that is perpendicular to the surface normal (vector n) at that point. This point is shown as point 2 on FIG. 4. In the next step, the inventive algorithm finds the closest point to point 2 that is on the bone surface, which is shown as point 3. To mimic registration operations in the operating room (OR), a random noise is added to the surface points (point 4 in FIG. 4). The added noise simulates a combination of errors including the segmentation error that generates the surface model, the digitizer error, and the possible presence of the soft tissue. The noise is assumed to have a normal distribution with a standard deviation of ±0.3 mm, and is added to the surface points along the surface normal. In a specific inventive embodiment, the computer simulation is performed on six cadaver cases and a foam bone case with various sizes, shapes and planning.

In certain inventive embodiments, each computer simulation trial performs the TKA registration and then calculates the translational and rotational errors in the implant space. In a specific inventive embodiment for each test case, the simulation trial is repeated 1000 times to simulate different bone POSEs in the OR and the point collection by different users. It is appreciated that other numbers of repeated trials may be used for each test case. Each simulator generates an output file, where the rows show the output for each run and the columns indicate the simulation number, the average and maximum point to surface distance, and the translational and rotational errors. The translational error includes medial/lateral errors, proximal/distal errors, anterior/posterior errors, or combinations thereof. The rotational error includes flexion/extension, valgus/varus errors, internal/external errors, or combinations thereof.

In certain inventive embodiments, the output files from both femur and tibia simulations are analyzed. The results for each of a series of runs are included in an output file. The percentage of trials that meet the acceptance criteria on the translational and rotational accuracy are recorded.

Figure 5:
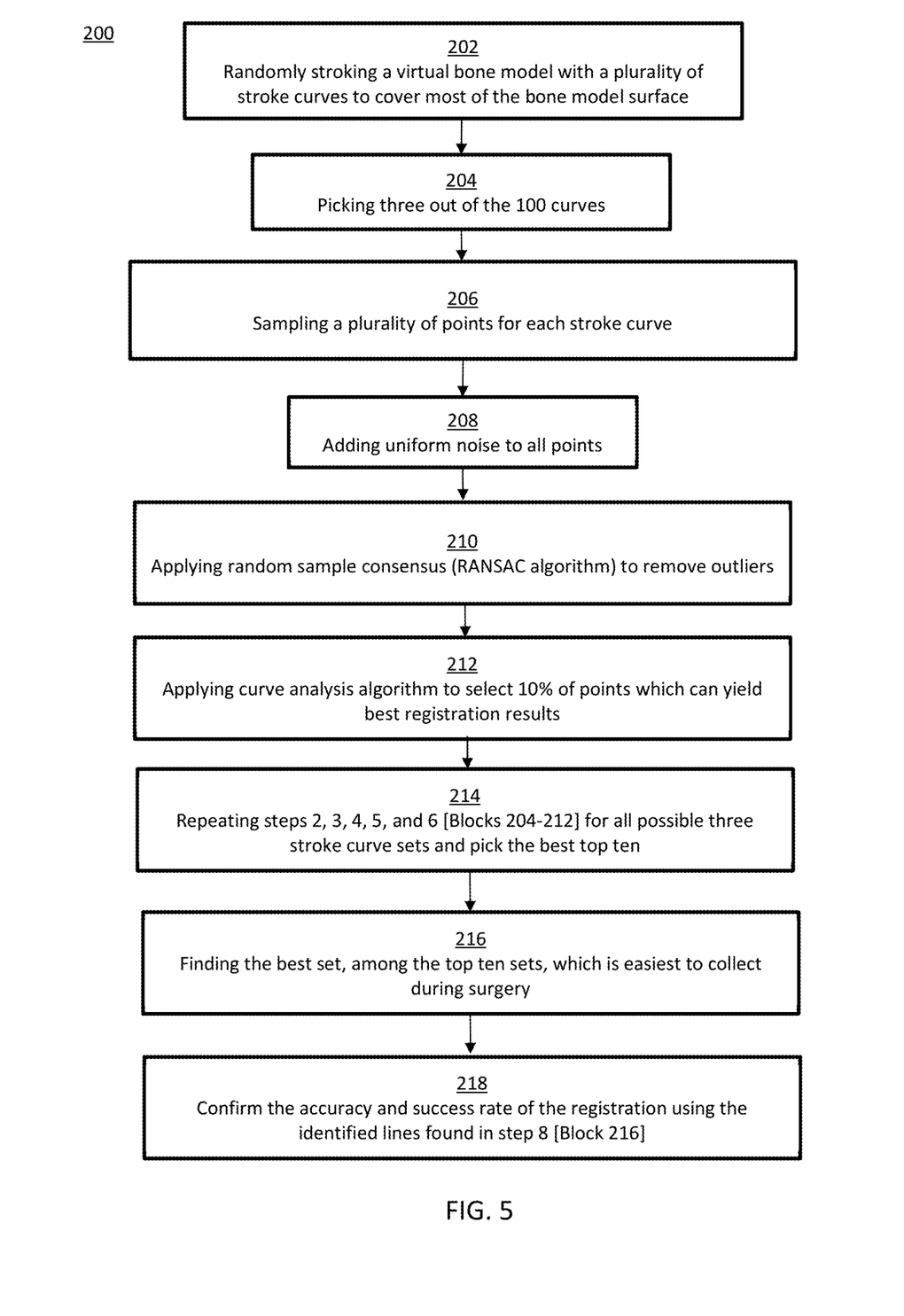
FIG. 5 depicts a method of bone registration where digitization of points is completely removed in accordance with embodiments of the invention.

In a specific inventive embodiment, a study result is accepted if greater than (≥) 95% of the simulated trials passed the TKA registration accuracy for each test case. A femur registration passes the accuracy criteria if, for example, the calculated medial/lateral, anterior/posterior and proximal/distal errors are less than 1 mm and flexion, extension, valgus, varus, internal and external values are less than 3.5 degrees, 1.5 degrees, 1.0 degrees, 1.0 degrees, 1.5 degrees and 1.5 degrees, respectively. It is appreciated that a user may define different thresholds for a passing bone registration. A tibia registration passes the accuracy criteria if the calculated medial/lateral, anterior/posterior and proximal/distal errors are less than 1 mm and flexion, extension, valgus, varus, internal and external values are less than 2.0 degrees, 1.5 degrees, 1.0 degrees, 1.0 degrees, 3.0 degrees and 3.0 degrees, respectively. Table 1 summarizes the acceptance criteria. Factors that are considered in adjusting a threshold illustratively include the target bone or joint, implant tolerances, bone density, and bone imperfections.

tration. The location of the three orthogonal lines is crucial and must provide an accurate representation of the bone. The more unique a feature is on the bone, the better the representation. Features such as curves/undulations/notches represent or identify specific regions on a bone better than a flat region because these curves are more unique to the bone. To identify these contour regions and register the bone, the following method 200 is used as shown in FIG. 5:

Simulation:
1. Randomly stroke a virtual bone model with a plurality of stroke curves (e.g., at least 100 curves) to cover most of the bone model surface, Block 202
2. Pick a subset of stroke curves (e.g. 3 to 10 curves) out of the plurality of curves, Block 204
3. For each stroke curve from the subset of stroke curves, sample a plurality of points, Block 206 (e.g. 150 points for each stroke curve)
4. Add uniform noise to all points, Block 208
5. Apply random sample consensus (RANSAC algorithm) to remove outliers, Block 210.
6. Apply curve analysis algorithm (to help find key points that can represent a curve) to select a fraction of points (e.g. 2 to 25%) which can yield best registration results, Block 212.
7. Repeat steps 2, 3, 4, 5, and 6 for all possible subsets of stroke curves and pick at least two top subsets of stroke curves that yield the best registration results, Block 214.

TABLE 1

| | Acceptance criteria | | | | | | | | | | | |
|---|---|---|---|---|---|---|---|---|---|---|---|---|
| Accuracy requirement | Medial (mm) | Lateral (mm) | Proximal (mm) | Distal (mm) | Anterior (mm) | Posterior (mm) | Flexion (deg) | Extension (deg) | Valgus (deg) | Varus (deg.) | Internal (deg.) | Ext. (deg.) |
| Femur | 1.0 | 1.0 | 1.0 | 1.0 | 1.0 | 1.0 | 3.5 | 1.5 | 1.0 | 1.0 | 1.5 | 1.5 |
| Tibia | 1.0 | 1.0 | 1.0 | 1.0 | 1.0 | 1.0 | 2.0 | 1.5 | 1.0 | 1.0 | 3.0 | 3.0 |

Based on the computer simulations for different digitization regions on the femur and tibia bones as describes above for embodiments of the inventive method, the following was determined:

The changes in the point collection for THA stem registration include:
1. The band region is removed
2. The new initial point is on the lesser trochanter instead of the band area
3. Two new regions are added on the inferior and superior femoral neck area. Two points on each region are collected (4 total).
4. Crest and medial to piriformis regions are merged into one region. Six points are collected in the merged region.
5. Intertrochanteric plane and lateral lesser trochanter regions are merged together. Four points are collected in the merged region.

The changes made in TKA femur regions include:
1. Removing 3 points from the band region
2. Adding 3 points to the proximal anterior region The changes made in TKA tibia regions include:
1. Added 1 point about 50 cm from the top of the tibia bone. This point is used as the fourth initial point.
2. Added two points to lateral epicondyle region.
3. Added a region on proximal anterior with 2 points.

In a specific inventive embodiment, the digitization of points is completely removed. In this inventive embodiment, three orthogonal lines are digitized on the bone for regis- 8. Among the at least two top subsets of stroke curves, also referred to herein as top subsets, find the best subset which is easiest to collect during surgery (the stroke curve set having the best overlap over the exposed region during surgery), Block 216.
9. Confirm the accuracy and success rate of the registration using the top subset found in step 8, Block 218.

In the operating room (OR) the following occurs:
1. A graphical user interface (GUI) guides a user to use a digitizer in a continuous collection mode to stroke the three or more lines as identified in the simulation (the lines correspond to the stroke curves in the top subset of stroke curves identified in the simulation).
   a. For each line digitized, the digitizer/system collects many more points than needed.
2. Select the points along each of the three or more lines based on the curvature of the bone to capture the critical contour shape information of each line to finish the registration.

Figure 6A:
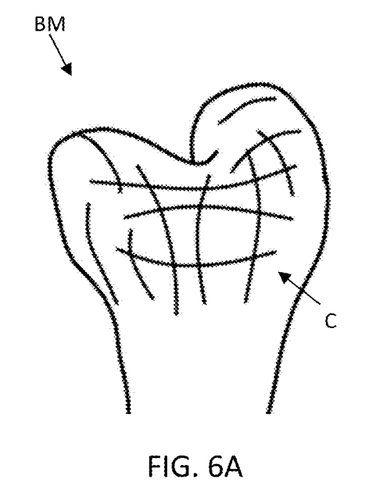
FIG. 6A depicts a plurality of stroke curves on a surface of a bone model.

To further illustrate the aforementioned method 200, FIGS. 6A to 6D provide a graphical representation of the method 200. FIG. 6A depicts a bone model having a plurality of stroke curves C randomly populated on the surface of the bone model BM. The plurality of stroke curves may be populated on the bone model BM using an algorithm. The algorithm may include code that rotates a plane (in three degrees-of-freedom for at least 100 different combinations of Rx, Ry, and Rz, to cover most of the bone region feasible for surgery) with respect to the bone model centroid.

Figure 6B:
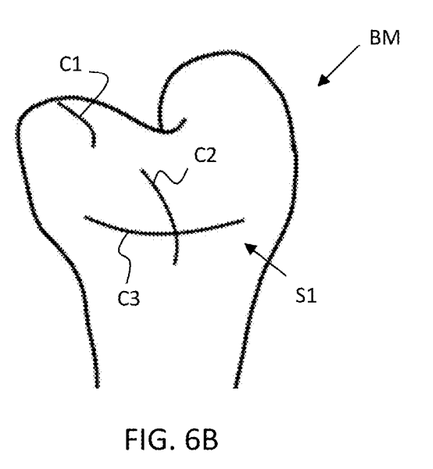
FIG. 6B depicts a first subset of chosen curves.
Figure 6C:
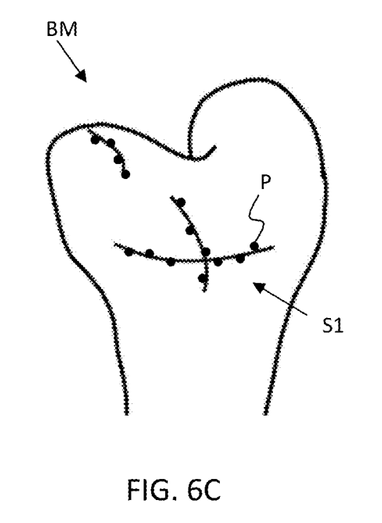
FIG. 6C depicts a plurality of points sampled relative to each stroke curve in the first subset.
Figure 6D:
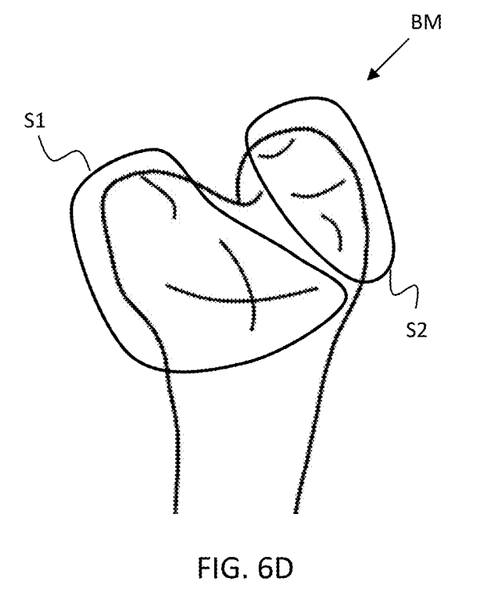
FIG. 6D depicts two top subsets of stroke curves, from which one will be chosen for registration.

The stroke curves are then defined by the intersection between the plane and the bone model BM. FIG. 6B depicts a first subset S1 of chosen stroke curves C, where the first subset S1 includes three stroke curves (C1, C2, and C3). FIG. 6C depicts the sampling of a plurality of points P for each stroke curve (C1, C2, and C3) corresponding to Block 206 of the method 200. With these points P, uniform noise is added (Block 208), outliers are removed (Block 210), and a curve analysis algorithm selects 2-25% of the points which can yield the best registration results (Block 212). The best registration results are determined by simulating the registration virtually to compare all combinations and then pick the best points based on their comparison to the ground truth. These steps are repeated for different subsets of stroke curves to identify at least two or more top subsets. FIG. 6D depicts an identified first top subset S1 and a second top subset S2 which yielded the best registration results corresponding to Block 214 of the method 200. Based on these two top subsets S1 and S2, top subset S2 is the more likely candidate to be used for registration as the curves/lines in the second top subset S2 is more likely to be exposed during surgery and the easiest to collect.

The elimination of the digitization of points and use of lines for bone registration in a robotic surgical procedure has the following advantages: a simpler and easier registration for the surgeon to complete; requires less time to register the bone; the use of a line can provide much more points for registration and capture the contour much more precisely and take less time to collect; improved accuracy and ultimately the success rate of the surgical procedure.

The methods 100 and 200 may further include the following steps. Prior to performing the simulations, an image data set of a bone may be acquired using an imaging modality such as CT, MRI, or ultrasound. A 3-D bone model may be generated from the image data set. This 3-D bone model is then used to perform the simulations above to identify the regions and/or curves/lines to perform the registration. As each patient is unique, the curvature and features of the bone are also unique. Thus, the methods 100 and 200 may be performed on a case-by-case basis to account for each patient's unique anatomy. However, it should be appreciated that the bones also have a generic shape, where the identified location for the regions and/or lines may be applicable for a plurality of different patients.

In particular embodiments, machine learning is implemented on several historical patient cases to determine the locations of the regions and/or lines that can successfully register any patient bone. This may be accomplished by performing the simulations described herein for a plurality of historical patient cases to identify patterns in the locations of the identified regions and/or lines, which can then be used for any future patient.

The methods 100 and 200 may further include the execution of a computer-assisted surgical procedure following the registration of the bone. In particular embodiments, a surgical plan having operational data (e.g., a cut-file, virtual boundaries, robot instructions) is defined and fixed relative to a 3-D model of the bone. Therefore, the registration procedure maps the surgical plan onto the bone in the coordinate system of the computer-assisted surgical device, which permits the surgical device to accurately execute or aid in the execution of the surgical plan on the bone.

Surgical System

Figure 7:
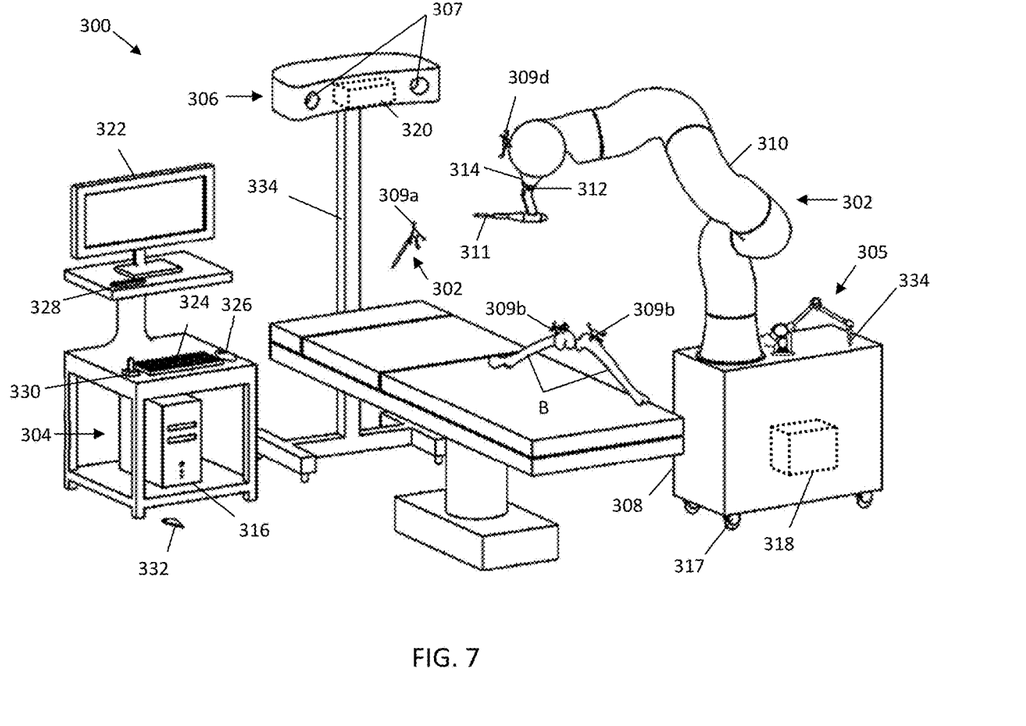
FIG. 7 depicts a robotic system in a surgical setting employing principles of the present invention in accordance with embodiments of the invention.

With reference to FIG. 7, an embodiment of a robotic surgical system 300 is shown capable of implementing embodiments of the inventive method described above. The aforementioned devices and methods are particularly useful for a robotic surgical system 300, which traditionally experience longer surgical times compared to manual techniques or techniques using hand-held tracked instrumentation.

The surgical system 300 generally includes a surgical robot 302, a computing system 304, and a tracking system 306.

The surgical robot 302 may include a movable base 308, a manipulator arm 310 connected to the base 308, an end-effector 311 located at a distal end 312 of the manipulator arm 310, and a force sensor 314 positioned proximal to the end-effector 311 for sensing forces experienced on the end-effector 311. The base 308 includes a set of wheels 317 to maneuver the base 308, which may be fixed into position using a braking mechanism such as a hydraulic brake. The base 308 may further include an actuator to adjust the height of the manipulator arm 310. The manipulator arm 310 includes various joints and links to manipulate the end-effector 311 in various degrees of freedom. The joints are illustratively prismatic, revolute, spherical, or a combination thereof.

The computing system 304 generally includes a planning computer 316; a device computer 318; a tracking computer 320; and peripheral devices. The planning computer 316, device computer 318, and tracking computer 320 may be separate entities, one-in-the-same, or combinations thereof depending on the surgical system. Further, in some embodiments, a combination of the planning computer 316, the device computer 318, and/or tracking computer 320 are connected via a wired or wireless communication. The peripheral devices allow a user to interface with the surgical system components and may include: one or more user-interfaces, such as a display or monitor 322 for the graphical user interface (GUI); and user-input mechanisms, such as a keyboard 324, mouse 326, pendant 328, joystick 330, foot pedal 332, or the monitor 322 that in some inventive embodiments has touchscreen capabilities.

The planning computer 316 contains hardware (e.g., processors, controllers, and/or memory), software, data and utilities that are in some inventive embodiments dedicated to the planning of a surgical procedure, either pre-operatively or intra-operatively. This may include reading medical imaging data, segmenting imaging data, constructing three-dimensional (3D) virtual models, storing computer-aided design (CAD) files, providing various functions or widgets to aid a user in planning the surgical procedure, and generating surgical plan data. The final surgical plan may include pre-operative bone data, patient data, registration data including the POSE of the points P defined relative to the pre-operative bone data, implant position data, trajectory parameters, and/or operational data. The operational data may include: a set of instructions for modifying a volume of tissue that is defined relative to the anatomy, such as a set of cutting parameters (e.g., cut paths, velocities) in a cut-file to autonomously modify the volume of bone; a set of virtual boundaries defined to haptically constrain a tool within the defined boundaries to modify the bone; a set of planes or drill holes to drill pins in the bone; or a graphically navigated set of instructions for modifying the tissue. In particular inventive embodiments, the operational data specifically includes a cut-file for execution by a surgical robot to autonomously modify the volume of bone, which is advantageous from an accuracy and usability perspective. The surgical plan data generated from the planning computer 316 may be communicated to the device computer 318 and/or tracking computer 320 through a wired or wireless connection in the operating room (OR); or communicated via a non-transient data storage medium (e.g., a compact disc (CD), a portable universal serial bus (USB) drive) if the planning computer 316 is located outside the OR.

The device computer 318 in some inventive embodiments is housed in the moveable base 308 and contains hardware, software, data and utilities that are preferably dedicated to the operation of the surgical device 302. This may include surgical device control, robotic manipulator control, the processing of kinematic and inverse kinematic data, the execution of registration algorithms (e.g., ICP), the execution of calibration routines, the execution of operational data (e.g., cut-files, the trajectory parameters), coordinate transformation processing, providing workflow instructions to a user, and utilizing position and orientation (POSE) data from the tracking system 306. In some embodiments, the surgical system 300 includes a mechanical digitizer arm 305 attached to the base 308. The digitizer arm 305 may have its own tracking computer or may be directly connected with the device computer 318. The mechanical digitizer arm 305 may act as with a digitizer probe 334 assembled to a distal end of the mechanical digitizer arm 305. In other inventive embodiments, the system includes a hand-held digitizer device 302.

The tracking system 306 may be an optical tracking system that includes two or more optical receivers 307 to detect the position of fiducial markers (e.g., retroreflective spheres, active light emitting diodes (LEDs)) uniquely arranged on rigid bodies. The fiducial markers arranged on a rigid body are collectively referred to as a tracking array (309a, 309b, 309c, 309d), where each fiducial marker array 309 has a unique arrangement of fiducial markers, or a unique transmitting wavelength/frequency if the markers are active LEDs. An example of an optical tracking system is described in U.S. Pat. No. 6,061,644. The tracking system 306 may be built into a surgical light, located on a boom, a stand 334, or built into the walls or ceilings of the OR. The tracking system computer 320 may include tracking hardware, software, data, and utilities to determine the POSE of objects (e.g., bones B, surgical device 302) in a local or global coordinate frame. The POSE of the objects is collectively referred to herein as POSE data, where this POSE data may be communicated to the device computer 318 through a wired or wireless connection. Alternatively, the device computer 318 may determine the POSE data using the position of the fiducial markers detected from the optical receivers 307 directly.

The POSE data is determined using the position data detected from the optical receivers 307 and operations/processes such as image processing, image filtering, triangulation algorithms, geometric relationship processing, registration algorithms, calibration algorithms, and coordinate transformation processing.

The POSE data is used by the computing system 304 during the procedure to update the POSE and/or coordinate transforms of the bone B, the surgical plan, and the surgical robot 302 as the manipulator arm 310 and/or bone B move during the procedure, such that the surgical robot 302 can accurately execute the surgical plan.

In another inventive embodiment, the surgical system 300 does not include an optical tracking system, but instead employs a mechanical arm 305 that may act as a tracking system 306 as well as a digitizer 334. If the bone is not tracked, a bone fixation and monitoring system may fix the bone directly to the surgical robot 302 to monitor bone movement as described in U.S. Pat. No. 5,086,401.

Other Embodiments

While at least one exemplary embodiment has been presented in the foregoing detailed description, it should be appreciated that a vast number of variations exist. It should also be appreciated that the exemplary embodiment or exemplary embodiments are only examples, and are not intended to limit the scope, applicability, or configuration of the described embodiments in any way. Rather, the foregoing detailed description will provide those skilled in the art with a convenient roadmap for implementing the exemplary embodiment or exemplary embodiments. It should be understood that various changes may be made in the function and arrangement of elements without departing from the scope as set forth in the appended claims and the legal equivalents thereof.

The invention claimed is:

1. A computer-implemented method to identify at least one digitization region on a bone model for use to register the bone model to a bone to a predefined registration accuracy, said method comprising executing on one or more processors:
    receiving a set of digitization regions located on the bone model based on expected exposed regions of the bone;
    performing a simulation simulating registration of the bone model to the bone to determine an accuracy of the registration when digitizing a plurality of points in each digitization region from the set of digitization regions;
    repeating the receiving and performing on different sets of digitization regions or combinations of digitization regions that are expected to be exposed to identify which digitization regions result in a simulated registration having the predefined registration accuracy; and
    storing at least one of the identified digitization regions for use when registering the bone model to the bone.

2. The method of claim 1 wherein the bone model is a patient-specific bone model, a cadaveric bone model, or a set of historical patient-specific bone models.

3. The method of claim 2 wherein the bone model is a patient-specific bone model.

4. The method of claim 1 further comprising registering the bone model to the bone using a plurality of digitized points on the bone in the at least one digitization region that meets the predefine accuracy requirement.

5. The method of claim 4 wherein a digitizer to computerized tomography (CT) registration matrix is calculated to register the bone model to the bone.

6. The method of claim 5 wherein 10 to 40 points are collected to calculate the registration matrix.

7. The method of claim 4 wherein the bone is a femur or tibia.

8. The method of claim 1 wherein a spatial position and orientation (POSE) of the bone model is simulated randomly with rotation angles of the bone limited to −179 degrees to 180 degrees about all three coordinate axes (X, Y, Z), and translation movement of the bone model is limited to +/−500 mm with respect to a coordinate system of a digitizer.

9. The method of claim 1 further comprising adding random noise to one or more of the plurality of points.

10. The method of claim 9 wherein the random noise simulates uncertainty introduced by a user when digitizing the one or more of the plurality of points, and wherein the random noise has a uniform distribution with a minimum value of −10 mm and a maximum value of 10 mm.

11. The method of claim 10 wherein adding random noise comprises moving a first point from the plurality of points by a random number chosen from the uniform distribution on a plane that is perpendicular to a first vector normal to a surface of the bone model at the first point to a point 2 from which the software determines a closest point 3 to point 2 on the surface of the bone model is determined; and wherein a second random noise is added to the point 3 along a second vector normal to the surface of the bone model to obtain a point 4.

12. The method of claim 1 wherein the predefined registration accuracy comprises translational and rotational errors between the bone model and the bone as registered in the simulation;
   wherein translational error includes medial/lateral, proximal/distal and anterior/posterior errors; and
   wherein the rotational error includes flexion/extension, valgus/varus, and internal/external errors.

13. The method of claim 12 wherein the predefined registration accuracy is met if: i) the medial/lateral, anterior/posterior and proximal/distal errors are less than 1 mm and flexion, extension, valgus, varus, internal and external errors are less than 3.5 degrees, 1.5 degrees, 1.0 degrees, 1.0 degrees, 1.5 degrees and 1.5 degrees, respectively; or
   ii) the medial/lateral, anterior/posterior and proximal/distal errors are less than 1 mm and the flexion, extension, valgus, varus, internal and external errors are less than 2.0 degrees, 1.5 degrees, 1.0 degrees, 1.0 degrees, 3.0 degrees and 3.0 degrees, respectively.

14. The method of claim 1 wherein the bone is subject to hip arthroplasty or knee arthroplasty.

15. The method of claim 1 wherein the one or more processors automatically receive the selections of the sets of digitization regions.

16. The method of claim 1 wherein the one or more processor receive the selections of the sets of digitization regions from a user.

* * * * *